(12) United States Patent
Rijke

(10) Patent No.: US 6,419,645 B1
(45) Date of Patent: Jul. 16, 2002

(54) DEVICE AND METHOD FOR EVALUATING INJURIES TO LIGAMENTS

(76) Inventor: Arie M. Rijke, 391 Ridge Lee Dr., Charlottesville, VA (US) 22903

( * ) Notice: Subject to any disclaimer, the term of this patent is extended or adjusted under 35 U.S.C. 154(b) by 0 days.

(21) Appl. No.: 09/704,382

(22) Filed: Nov. 2, 2000

(51) Int. Cl.[7] .................................................. A61B 5/00
(52) U.S. Cl. ...................................................... 600/587
(58) Field of Search ................................ 600/587, 592, 600/594, 595

(56) References Cited

U.S. PATENT DOCUMENTS

| | | |
|---|---|---|
| 4,232,681 A | 11/1980 | Tulaszewski |
| 4,583,555 A | 4/1986 | Malcom et al. |
| 4,969,471 A | 11/1990 | Daniel et al. |
| 5,156,163 A | 10/1992 | Watkins et al. |
| 5,462,068 A | 10/1995 | Rijke et al. |
| 5,724,991 A | 3/1998 | Rijke et al. |
| 5,911,695 A | 6/1999 | Watkins et al. |
| 6,013,039 A | 1/2000 | Watkins et al. |

OTHER PUBLICATIONS

Clinical Orthopaedics, vol. 210, Sep. 1986 Arie M. Rijke, M.D. Ph. D.; Barrington Jones, M.B., B. Ch., F.R.C.R. Pieter A. M. Vierhout, M.D. Ph. D. J. B. Lippincott Co. U.S.A.

The American Journal of Sports Medicine, vol. 16, No. 3, 1988 pp. 256–259 Arie M. Rijke, Barrington Jones, Pieter A. Vierhout.

Acta Radiologica, vol. 31, 1990, pps. 151–155 From the Department of Radiology, University of Virginia Health Sciences Center, Charlottesville, VA and The Department of Surgery, University Hospital, Leiden, The Netherlands. A. M. Rijke and P. A. Vierhout.

*Primary Examiner*—Max Hindenburg
(74) *Attorney, Agent, or Firm*—Sheldon H. Parker; Kimberly O. Snead

(57) ABSTRACT

A new process and device are described which together make it possible to quantify and monitor the percentage of remaining or regained ligament function by externally measuring anatomical reference points using electronic sensors which have been added to existing ligament stress devices and then applying mathematical models to these measurements, thereby eliminating the need for x-rays or other imaging modalities. The device is compact and portable and can be operated by a technician, eliminating the need for the physician to conduct the test. The information generated by the device and the method is presented in an easy to read clinical format eliminating the need for the physician to make computations in order to make a diagnosis.

21 Claims, 5 Drawing Sheets

DEVICE AND METHOD FOR EVALUATING INJURIES TO LIGAMENTS

FIELD OF THE INVENTION

A medical device and method are described which provide quantitative information on the type and extent of injury to the ligaments of the ankle, elbow, knee and shoulder without the need for x-rays or other imaging modalities. The invention combines stress equipment for ligaments with electronic sensors, a computer interface and analytical software containing predictive functions to provide the care provider with an accurate diagnosis of ligament injury.

DESCRIPTION OF THE PRIOR ART

Injuries to the ligaments of the ankle and the knee have been rising sharply as our health-conscious society has taken to physical exercise and athletics. Estimates for ankle injury in the U.S suggest that as many as 10% of office and emergency room visits (approximately 20,000 ankle examinations per day or approximately 9 million per year) involve the ankle joint, of which the vast majority are lateral ankle sprains. The numbers of cruciate and collateral ligament injuries are less well known but have been increasing everywhere over the past decade. In the United States, well over 10,000 anterior cruciate ligaments are ruptured on the ski slopes alone each year. Joint injuries as a whole contribute greatly to the number of medical examinations. Although some of these injuries are mild and can be self managed following an initial diagnostic workup, they nonetheless cause significant morbidity and loss of work productivity as they affect mostly the 15- to 45-year old age group.

The initial workup of ligament injury involves, after osteochondral fractures or other complications have been excluded, an accurate assessment of the extent of ligament damage. Determining the extent of the damage to ligaments allows the physician to make the appropriate choice of treatment, including whether or not surgery is required. Equally important is monitoring the functional improvement in order to assess the success of rehabilitation programs.

The typical methods for evaluating damage to ligaments are physical examination, stress examinations including stress radiography, and occasionally magnetic resonance imaging (MRI), computerized axial tomography (CAT) scan and arthroscopy. Although MRI can directly image the affected ligament, it is unable to assess function properties. Whereas each of these diagnostic tools has its own intrinsic value, and contributes to the total assessment of the actual injury, it is evident that, together, they also markedly add to the total cost.

Current technologies for assessing joint laxity include arthrometers and goniometers and they are limited in their ease of use and diagnostic capability. A leg positioning device for taking x-rays is described in U.S. Pat. No. 4,232,681 and is one example of an early device for diagnosing ligament injury. The information contained in this patent is incorporated by reference in its entirety. This device, sold as the GA-II/E Stress Device by the Telos Corporation (Marburg, Germany) enables the examiner to position the limb and apply a measured force to the joint but requires the physician to take x-rays in order to assess the likelihood of injury to the ligament. The GA-II/E is capable of positioning multiple joints including the ankle, the knee and the shoulder for x-ray analysis of their ligaments. The positioning of the extremities to evaluate ligaments is shown in the users manuals provided by Telos Corporation and entitled Telos Stress Device Users Manual Shoulder-Positioning-Device for Standardized Axial x-rays and Stress Radiographs. These publications are incorporated by reference in their entirety. A wrist holding attachment described in U.S. Pat. Nos. 5,724,991 and 5,462,068 expands the use of the GA-II/E to the elbow. These patents are incorporated by reference in their entirety. However, this diagnostic technique is time consuming, is less reproducible, is not automated and requires the diagnostician to make measurements from the x-rays and calculate joint laxity by graphing the measured displacements.

Another technology currently in use to measure joint laxity includes the knee and shoulder testers sold by the Medmetric Corporation (San Diego, Calif.). These devices include the KT 1000 and KT 2000 knee testers and are described in U.S. Pat. Nos. 4,969,471 and 4,583,555. A shoulder tester is also described in U.S. Pat. No. 5,911,695 and a patella displacement tester is described in U.S. Pat. Nos. 5,156,163 and 6,013,039. These patents are incorporated by reference as though reproduced in their entirety. The devices described in these patents use force displacement measurements combined with linear displacement of the appropriate bones to provide diagnostic information on joint laxity. Each of these devices is limited to the assessment of the laxity of a single ligament, and therefore the purchase of multiple systemswould be required to test the various joints resulting in an increase in the cost to the physician and the patient. Further, the only information that is provided to the physician is the actual measurement of the force and the displacement, and the physician would be required to further manipulate this information in order to arrive at a diagnosis in terms of percentage tear.

Development of new technologies and approaches and/or optimization of any of the existing techniques—while providing an improved, the same or at least an acceptable level of care is required to significantly reduce the cost of the diagnostic phase. If in this process, these new technologies/approaches can be adopted to quantitatively assess ligament recovery under any of the existing rehabilitation programs, a new procedure may have emerged that is capable of delivering essential diagnostic and therapeutic information at significantly lower cost.

SUMMARY OF THE INVENTION

The novel process of the invention employs a modification of commercially available stress equipment used to assess trauma-induced laxity in a variety of joints including the ankle, knee, elbow and shoulder. Electronic sensors attached to the stress equipment measure the location of specific anatomical reference points. These measurements are used in mathematical models to calculate the percentage of remaining or regained function in the traumatized ligaments without the use of imaging modalities or invasive procedures.

Computer software presents the results and diagnosis in a clinical format. The examination is performed in a matter of minutes and at a fraction of the usual cost by a trained technician and does not require a hospital setting. The preferred embodiment of the assembled device is available in a lightweight briefcase-sized portable unit and can be operated wherever a PC or laptop is available.

The invention improves standard graded stress radiographic exams to eliminate the need for x-rays or other imaging modalities, and it makes ligament stress exams accessible to non-radiological personnel, such as athletic trainers, without loss in diagnostic accuracy.

DETAILED DESCRIPTION OF THE INVENTION

Figure 1:
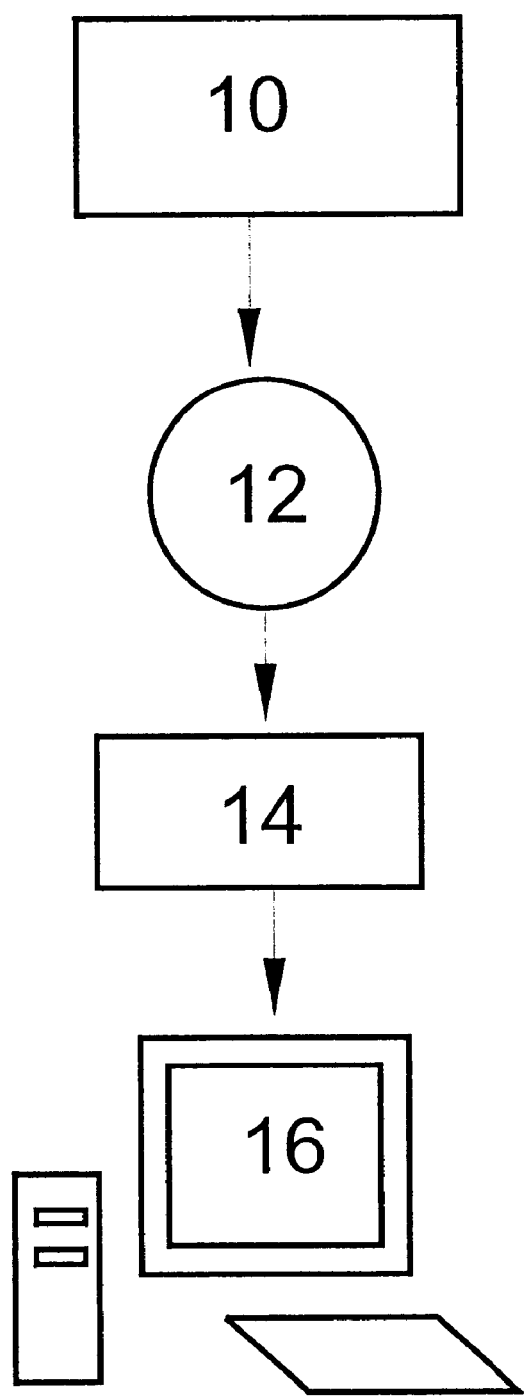
FIG. 1 is a flow diagram of the generic process involved in diagnosing ligament injury.

FIG. 1 shows a flow diagram of the generic diagnostic process entailed by the invention. The extremity to be tested is appropriately positioned in a stress device 10 and a force is applied to the joint of interest (ankle, knee, elbow or shoulder). The displacement caused by the applied force is read by incremental encoders 12 and a digital or analog signal is generated. An interface board 14 reads the signal and causes conversion to a digital signal if necessary. The interface board processes the force displacement signal and sends the information to a computer processor 16 which analyzes the information using the trigonometric functions described below and presents the information in a clinical format.

With this generic process in mind, the invention comprises two main components.

Component I: Electronic sensors are attached at appropriate locations to commercially available ligament stress equipment. The sensors measure the change in the location of anatomical reference points in an extremity as a function of a range of measured forces which are exerted on a specific anatomical reference point in the joint being tested. It should be noted that the present invention is not limited to any particular type of sensor.

Two types of sensors are attached to the stress device in addition to the existing sensor which measures force applied by the pressure plate. Rotary encoders are attached at each of the two points where the ankle piece can be inserted into the stress device, and these encoders measure the rotation of the ankle piece. A shaft on the bottom of the ankle holding piece slides into a hole on the Telos device; the entire ankle holding piece can swivel on this shaft. The rotary encoders are located at the base of this shaft, so that they can measure the rotation of the shaft. A linear encoder is attached to the device in line with the pressure plate to measure the distance that the pressure plate travels while the force is being applied. To test the ankle requires rotational measurements from the rotary encoder, distance measurements from the linear encoder, and measurements of the force applied by the pressure plate. To test knee, elbow, and shoulder ligaments, only the distance measurements from the linear encoder and the measurements of the force applied by the pressure plate are required. The use of these types of sensors enables the interface board to digitize and communicate with the diagnostic software.

The use of electronic sensors linked to an interface board allows the diagnostic software to acquire digital input of the measurements from the sensors. Electrical communication between encoders and the interface board can be conveniently established using standard telephone wiring, but adaptations to data transmission using infra-red or any other wireless or wired technology are well within the scope of our new technology.

Component II:—Mathematical formulas manipulate the data gathered by the sensors in Component I to compute the change in the talar tilt angle of the ankle joint or the relative displacement of the bones in the knee, shoulder, or elbow joint.

When the ankle is tested in a stress device, the talar tilt angle is calculated which makes it possible to determine the remaining lateral or medial ligament function using the Graded Stress Technique (GST) system. GST was first applied to ligaments as published by Rijke and colleagues in the journal Clinical Orthopaedics, Vol. 210, September, 1986, which is incorporated herein by reference in its entirety. Such analysis has correlated well with arthrography and operative techniques as described in Rijke et al., The American Journal of Sports Medicine, Vol. 16, No. 3, 1988, pps.256–259 and in Rijke & Vierhout, Acta Radiologica, vol. 31, 1990, pps. 151–155 which are incorporated herein by reference in their entireties.

The formulas used to calculate the talar tilt reflect the specifics of the human leg and ankle anatomy as well as the dynamics of the stress equipment. Specifically, the distance from the counter plate B to the ankle joint (distance BC in FIG. 2B and distance BE in FIG. 2C, respectively) is measured for each patient. The distance between the midpoints of the two extension arms on the stress device is also measured. This is distance AB in FIGS. 2B and 2C, In addition, the distance between the midpoint of the threaded spindle holding the pressure plate and the midpoint of the extension arm holding the counter plate near the knee. is measured. This is distance $c_1$ in FIG. 2C. The formulas also allow for the unsuspected presence or unknown extent of subtalar instability or hypermobility in the patient.

Figure 2A:
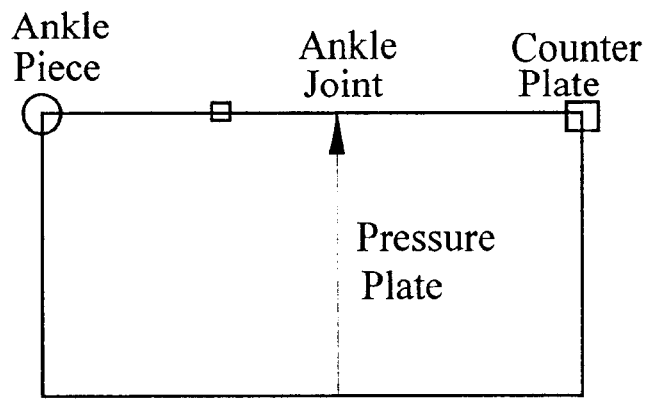
FIG. 2 represents a simplified view of the orientation of the invention when used on the ankle and the angular changes during testing that occur due to ankle injury.

FIG. 2A is a schematic representing the relationship between the ankle holding piece, the ankle joint, the counter plate, and the direction of the applied force when testing the ankle for lateral ligament insufficiency in a stress device.

Figure 2B:
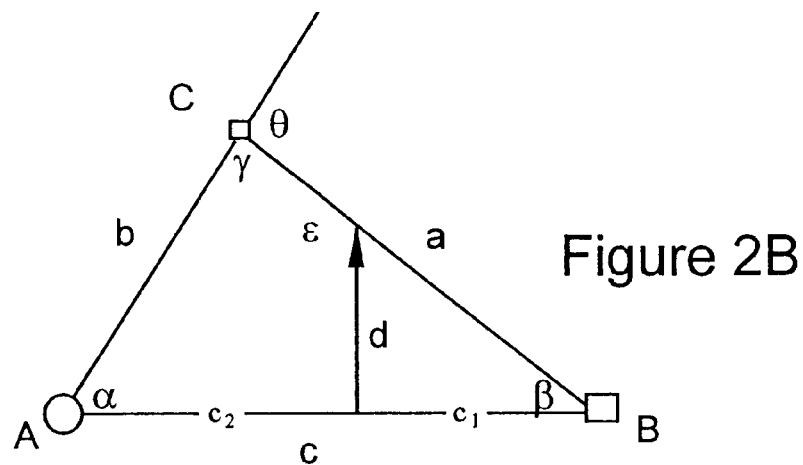

In FIG. 2B, AB represents the distance between the position of the ankle piece and the counter plate near the knee and C is the position of the ankle joint. The pressure plate is positioned 2 cm proximal to the ankle joint, a distance $c_1$ from the counter plate. When a force F is applied, which involves a distance d traveled from the crossbar, the ankle joint will tilt with an angle $\theta$. This angle equals:

$$\theta = \alpha + \beta = \alpha + \arctan(d/c_1) \quad \text{(Equation 1)}$$

As force is applied on the pressure plate, there is a continuous reading of a and of the displacement of the pressure plate. When allowance is made for mobility in the subtalar joint, whether physiological or pathological, FIG. 2C applies. The talar tilt angle then follows from:

$$\cos \epsilon = [d_1 + e\cos(\alpha+\beta)]/[(d_1^2 + e^2 + 2d_1 e\cos(\alpha+\beta)]^{1/2} \quad \text{(Equation 2)}$$

Figure 2C:
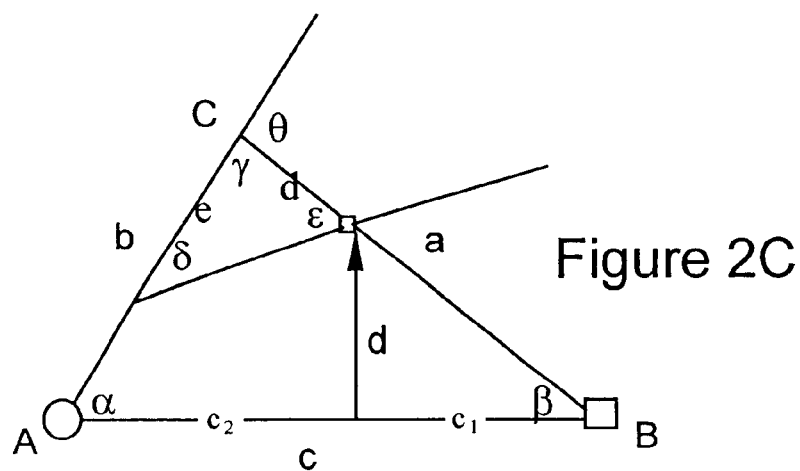

Here, $\epsilon$ represents the talar tilt angle and e represents the distance between the tibiotalar joint and the talocalcaneal joint, averaging 25.7 mm. The subtalar tilt angle $\delta$ subtends the virtual distance $d_1$. When the applied force causes a subtalar tilting of $\delta$ degrees, the talocalcaneal joint will separate laterally and thereby increase the joint space by a distance DE–DC as shown in FIG. 2C. Calculation of $\epsilon$ from Equation 2 then provides a value to be placed into GST in order to determine ligament injury.

Subtalar instability and hypermobility are uncommon insufficiencies of the ligaments of the foot involving, respectively, tears and overstretching of the talocalcaneal ligaments such as the cervical and interosseous ligaments as well as the capsule of the subtalar joint. Diagnostically, subtalar insufficiency is difficult to distinguish from the much more common lateral ankle sprain with symptoms and signs overlapping.

The software directly distinguishes between talar tilt θ and subtalar tilt δ and thereby make possible a prompt diagnostic distinction between the two entities—without performing any additional examinations. This is because the subtalar tilt δ equals the difference between the talar tilt θ, computed according to Equation 1 arid the talar tilt & computed according to Equation 2. This relationship is expressed in Equation 3:

$$\text{Subtalar tilt } \delta = \theta - \epsilon \qquad \text{(Equation 3)}$$

The talar tilt θ according to Equation 1 assumes the talocalcaneal joint to be rigid whereas the talar tilt according to Equation 2 assumes a measure of mobility in this joint. Normal subtalar joints show a finite value for δ, equaling that of the opposite foot. Hypermobility will show as slack in the talocalcaneal ligaments but will show normal viscoelastic behavior of these ligaments in the higher ranges of forces applied. Instability, on the other hand, is associated with partial or complete tears of the ligaments. This will show as abnormal force—subtalar tilt relationships from which the extent of tear including complete tears can be diagnosed accurately.

Previously, subtalar instability/hypermobility could only be subjectively assessed, and then only in experienced hands, by manually applying force and recording the lateral talocalcaneal joint separation on x-rays. The software and trigonometric formulas described in the instant invention will permit a graphical representation on computer screen of the force vs. subtalar tilt relationship and compute ligament slack and extent of talocalcaneal ligament tear as part of the specific software algorithms.

The capability to distinguish diagnostically between talar- and subtalar insufficiency was hitherto exceedingly difficult and yielded only questionable results. The instant invention not only facilitates the determination of both types of insufficiency in one, non-invasive examination, but also distinguishes between subtalar hypermobility and subtalar instability with quantitative assessment of ligament slack in the former and percentage of tear in the latter case.

Figure 3:
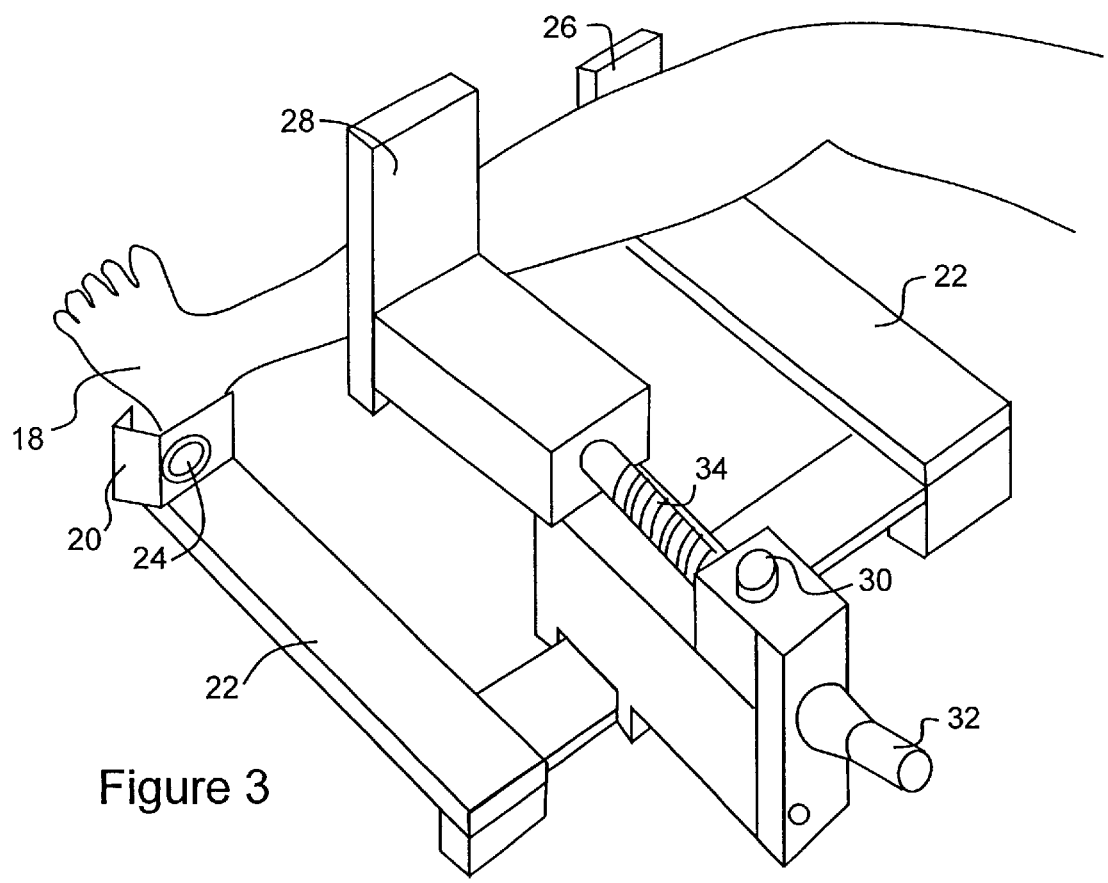
FIG. 3 represents the configuration of the stress device for measurement of ankle ligament injury.

FIG. 3 is a graphic representation of a leg positioned in a Telos stress device to determine injury to the ligaments of the ankle. A foot 18 is placed in the ankle holding piece 20 and attached to an extension arm 22. The ankle holding piece 20 is free to rotate around a pin that affixes the ankle holding piece 20 to the extension arm 22. A rotary encoder 24 is attached between the ankle holding piece 20 and the extension arm 22 to measure the rotation of the ankle holding piece 20. A counter support 26 is attached behind the leg and the pressure device 28 is adjusted to impact the leg by pressing the release button 30 and sliding the pressure device 28. A diagnosis begins by adjusting the turning grip 32 such that the pressure device 28 is moved along a threaded spindle 34 and force is applied to the limb.

Figure 4:
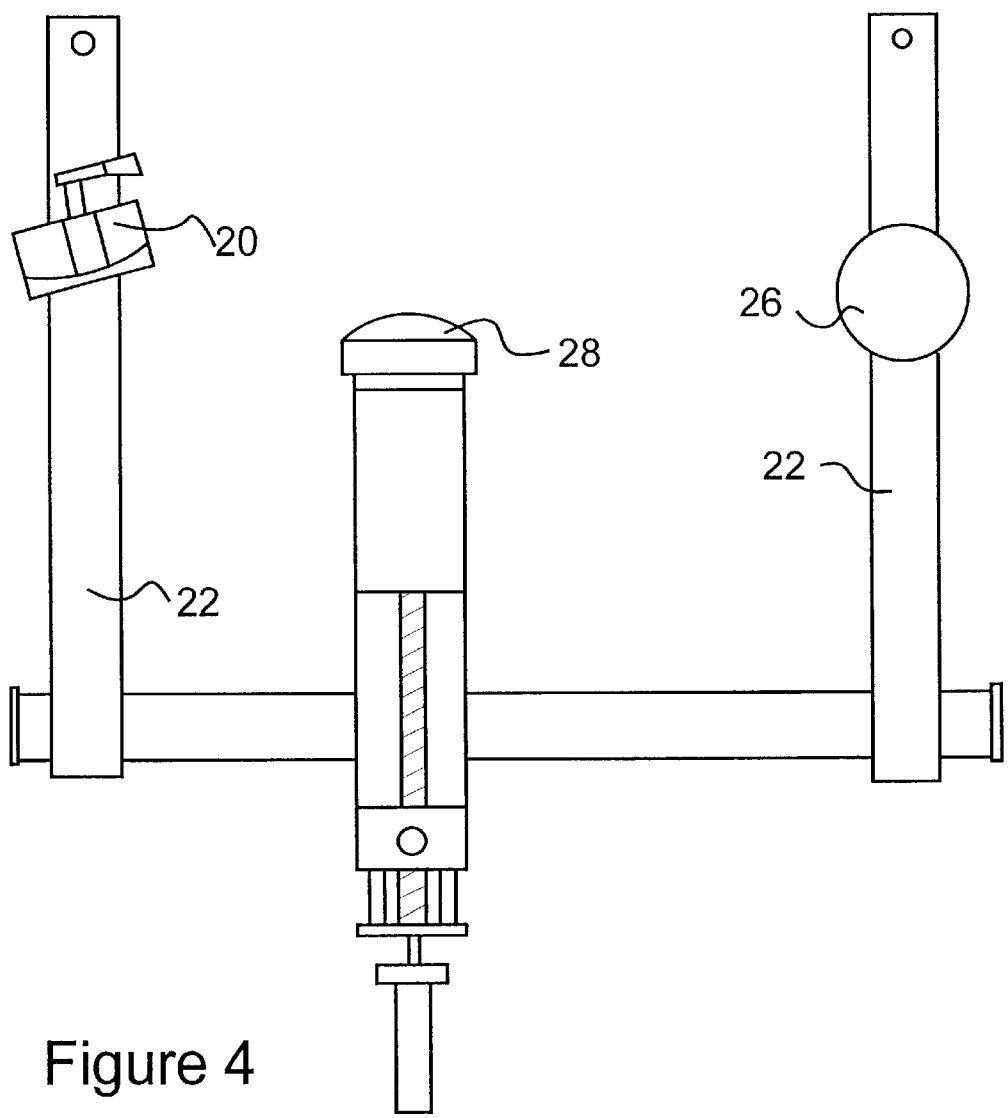
FIG. 4 shows the configuration of the stress device when it is tested for anterior calcaneal ligament injury.

FIG. 4 shows the orientation of the ankle holding piece 20, the counter support 26 and the pressure device 28 when the right ankle is tested for anterior calcaneal ligament injury.

Figure 5:
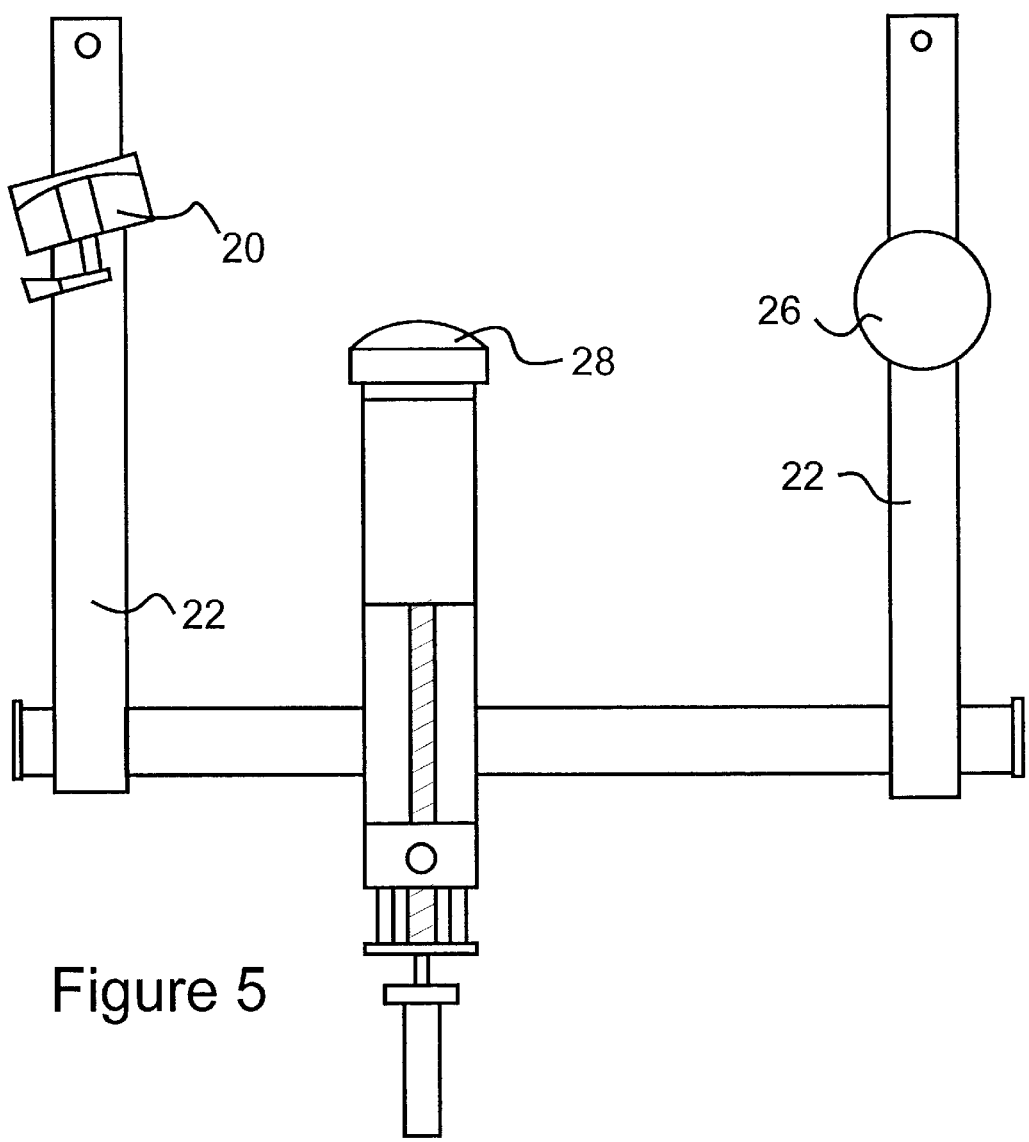
FIG. 5 shows the configuration of the stress device when it is tested for deltoid ligament injury.

FIG. 5 shows the orientation of the ankle holding piece 20, the counter support 26 and the pressure device 28 when the left ankle is tested for deltoid ligament injury.

In the knee and elbow joints, only force versus linear displacement relationships need be measured to acquire the relevant diagnostic information even though different anatomical parameters apply for each joint.

In order to assess the extent of injury to the collateral ligaments of the knee and elbow conventional stress devices attempt to measure the stretching of the ligament which is located opposite the point at which the measured force is applied. In traditional Graded Stress Radiography this is accomplished by measuring the unilateral widening of the joint space seen on an x-ray. Our modification allows us to determine the unilateral joint space widening by instead measuring the distance traveled by the pressure plate. For the range of forces typically applied to take GST measurements, the widening of the joint space has now been found to be sufficiently linearly proportional to the distance traveled by the pressure plate to make this measurement useful for the GST system. Therefore an accurate diagnosis of the percentage of tear in the collateral ligaments is calculated by inserting the distance traveled by the pressure plate into the GST formula instead of the x-ray derived measurement of the joint space widening.

Assessing posterior cruciate ligament injuries requires a measurement of the subluxation of the joint rather than the widening of the joint space, and thus a different position of the pressure plate and the counter plates in the conventional stress device. The amount of translation in the joint has also been found to be sufficiently proportional to the distance traveled by the pressure plate to make this measurement useful for the GST system, so this distance can once again be used to compute the extent of injury using the GST system.

The integrity of the medial elbow ligaments can be accurately assessed using standard Telos stress equipment and recording the unilateral widening of the joint space on x-rays. While performing this examination, it is important to fixate the wrist in supination, and a special wrist fixation device has been designed and patented (U.S. Pat. Nos. 5,724,991 and 5,462,068) to do this job. Here again, the unilateral widening of the joint space has now been found to be sufficiently linearly proportional to the distance traveled by the pressure plate to make this measurement useful for the GST system, so this distance call once again be used to compute the extent of injury using the GST system without the need for x-rays.

Since 1996, Telos equipment, originally designed for stress examination of ankle and knee ligaments, includes an optional shoulder positioning device that features a support bar on which the pressure plate can be mounted. As a result, a force from the pressure plate can be applied in a correct anatomical position and direction to measure (and record on x-rays) humero-glenoid subluxation, in a manner similar to that in which the laxity of knee ligaments are routinely measured. Here again, the force—displacement relationship in suspected shoulder ligament insufficiency can be recorded by our new technology using the linear encoder mounted on the pressure plate and processing the data by our software without the use of x-rays.

In a very similar manner, the Shoulder tester as described in U.S. Pat. No. 5,911,695 assigned to Medmetric Corporation of San Diego Calif., is a modified KT model that operates on the same principle of applying force and measuring the resultant movement in the joint. Our software is capable of measuring the force—displacement relationship as recorded by the Shoulder tester and computing the percentage ligament damage (or recovery) in the same fashion as is done for knee ligaments using the KT2000 model in conjunction with our software.

It is evident from the above descriptions that data from force—displacement measurements to determine laxity in the ligaments of any joint, examined by any of the above equipment, can be processed by our system to calculate the percentage rupture or recovery rather than simple laxity. This is regardless of whether specific equipment routinely requires x-rays such as Telos or movement indicators such as the KT models including the Shoulder tester. It also means that our system is capable of assessing ligament damage in conjunction with new, still-to-be designed equipment, that will use force—displacement measurements as their basis for ligament function analysis. Such stress devices, or their accessories, that are presently non-existing or incapable of quantitatively evaluating the ligaments of small joints, in the hand/wrist or the foot, for instance, are within this category.

The geometric calculations and the GST calculations required in this system are performed by proprietary software. One embodiment of this software is copyrighted under registration number TXu 938-577, incorporated herein by reference in its entirety. This software can be used in PC and Macintosh compatible computers including but not limited to desktop computers, laptops, palm computers and other portable computing devices. The code has been written to be very user-friendly and compatible with clinical practice.

The software performs all calculations necessary to arrive at the diagnosis, expressing the post-injury condition of the involved ligaments in terms of percentage remaining function or, if on rehabilitation, recovery of function. In addition, the program allows easy access to all data gathered and processed for comparison, reproducibility or cross checking for operator errors in the event of unexpected results. Users will also be able to access a national database compiled by the collective user program for comparison with gender/age related groups. The preceding examples are provided for descriptive purposes solely and are not meant to limit the embodiments of the invention. Other applications of the device will become apparent to those of ordinary skill in the art.

What is claimed is:

1. A device for determining ligament injury, comprising:
   a ligament stress member,
      said ligament stress member having a pressure member and at least one pair of counter members, said pressure member and said pair of counter members being positioned relative to each other such that said pressure member can be positioned proximate a body joint and each counter member can be positioned proximate a bone on each side of said joint,
   a distance movement sensor and a force sensor associated with said pressure member,
   a computer having digital data storage,
   communication means for providing data communication between said computer, and said
   distance movement sensor and said force sensor,
      said computer having calculation means, said calculation means calculating the extent of ligament injury from data from said distance movement sensor and said fore sensor.

2. The device of claim 1, wherein said joint is a knee, an elbow or a shoulder.

3. A device for determining ankle ligament injury, comprising:
   a ligament stress member,
   said ligament stress member having a pressure member and a counter member and an angular motion member rotatable relative to said pressure member,
   said pressure member, said counter member and said angular motion member being positioned relative to each other such that said pressure member can be positioned proximate an ankle and each of said counter member and said angular motion member can be positioned on each side of said ankle,
   a distance movement sensor associated with said pressure plate,
   an angular position sensor associated with said angular motion member, said angular movement sensor generating progressive data,
   a computer having digital data storage,
   communication means for providing data communication between said computer and said distance movement sensor angular position sensor,
      said computer having calculation means, said calculation means calculating ligament injury from data from said distance movement sensor and said progressive data from said angular position sensor,
      said computer having talar tilt calculation means for determining ankle ligament injury.

4. The device of claim 3, wherein said computer further comprises means for calculating the subtalar tilt angle from the angular position of said angular member and from the distance movement of said pressure plate sensed by said distance movement sensor.

5. The device of claim 3, further comprising a digital data storage member, means for progressively storing said data from said distance movement sensor and said progressive data from said angular position sensor.

6. The device of claim 5, wherein said computer further comprises means for calculating the subtalar tilt angle from the angular position of said angular member and from the distance movement of said pressure plate sensed by said distance movement sensor.

7. A method of diagnosing a ligament condition at a body joint having a first bone articulating with a second bone, comprising the steps of:
   a—positioning said first bone within a diagnostic device,
   b—positioning said second bone relative to said first bone,
   c—pressing a pressure member against said body joint between said first bone and said second bone,
   d—generating a first signal that corresponds to the distance traveled by said pressure member while said pressure member is being pressed against said joint,
   e—inputting said first signal to a computer, and
   f—processing said first signal in said computer and calculating the ligament condition of at least one ligament associated with said joint.

8. The method of claim 7, wherein said pressure member is positioned relative to said first bone and said second bone to cause said first bone to move relative to said second bone and to thereby create a subluxation at said joint between said first bone and said second bone.

9. The method of claim 8, further comprising the step of generating a second signal that corresponds to the pressure applied by said pressure member against said joint, inputting said second signal to said computer and generating a visual numerical display.

10. The method of claim 7, wherein said calculating of the condition of said ligament produces a visual display that represents the condition of said ligament.

11. The method of claim 7, further comprising the step of computer generating a visual display of the slope of a line that represents the pressure applied by said pressure member against said joint plotted against the distance traveled by said pressure member while said pressure member is being pressed against said joint.

12. The method of claim 8, wherein said diagnosing of a ligament condition includes the comparing the diagnosis of a patient's injured joint with said patient's uninjured joint, and further comprising the step of performing steps a, b, c and d with both a patient's injured joint and uninjured joint, and calculating a comparison of the ligament condition at said uninjured with the ligament condition at said injured joint.

13. The method of claim 8, wherein said joint is a knee, an elbow or a shoulder.

14. The method of claim 7, further comprising the step of generating a second signal that corresponds to the pressure applied by said pressure member against said joint, inputting said second signal to said computer, generating a first digital data from said first signal and a second digital data from said second signal, calculating from said first digital data and said second digital data, the slope of a line that represents the pressure applied by said pressure member against said joint plotted against the distance traveled by said pressure member while said pressure member is being pressed against said joint and generating slope data, calculating from said slope data the condition of a ligament at said joint.

15. The method of claim 14, wherein said pressure member is positioned relative to said first bone and said second bone to cause said first bone to move relative to said second bone and to thereby create a subluxation at said joint between said first bone and said second bone.

16. The method of claim 8, wherein said joint is a patient's ankle, and flier comprising the steps of:

providing angular rotation of said patient's lower leg bones relative to said patient's talus, sensing said angular rotation and generating progressive data relative to said angular rotation, progressively sensing the distance traveled by said pressure member corresponding to progressive angular rotation, said first signal being progressive distance traveled data, processing said progressive distance traveled data and progressive angular rotation data signal in said computer and calculating the ligament condition of said ankle.

17. The method of claim 16, further comprising the step of calculating talar tilt from said calculation means for determining talar tilt from said progressive angular rotation data and from progressive distance traveled data.

18. The method of claim 17, further comprising the step of calculating the subtalar tilt angle for each of a plurality of angular rotations of said patient's talus and from each of a plurality of corresponding angular rotations and distance movements of said pressure plate, generating subtalar tilt data, and calculating said ligament condition of said ankle using said subtalar tilt data.

19. The method of claim 7, wherein said diagnosing of a ligament condition includes the comparing the diagnosis of a patient's injured joint with said patient's uninjured joint, and further comprising the step of performing steps a, b, c, and d with both a patient's injured jointed with the ligament condition at said injured joint.

20. The method of tracking a patient's ligament condition comprising, for each joint of a pair of joints, wherein each joint includes a first bone articulating with a second bone, a—positioning said first bone within a diagnostic device, b—positioning said second bone relative to said first bone, c—pressing a pressure member against said body joint, d—generating a first signal that corresponds to the distance traveled by said pressure member while said pressure member is being pressed against said joint, inputting said first signal to a computer, e—generating a second signal that corresponds to the pressure applied by said pressure member, and processing said first and said second signal in said computer and generating digital data corresponding to said first signal and said second signal, f—storing said digital data in a database, periodically repeating steps (a) through (e) for at least one joint of said pair of joints, and generating periodic data, storing said periodic data in said database.

21. The method of producing a statistical database of body joint measurements, comprising, for at least one joint of a pair of joints, wherein each joint includes a first bone articulating with a second bone, the steps of:

a—positioning said first bone within a diagnostic device, b—positioning said second bone relative to said first bone, c—pressing a pressure member against said body joint, d—generating a first signal that corresponds to the distance traveled by said pressure member while said pressure member is being pressed against said joint, inputting said first signal to a computer, e—generating a second signal that corresponds to the pressure applied by said pressure member, and processing said first and said second signal in said computer and generating digital data corresponding to said first signal and said second signal, f—storing said digital data in a database, g—repeating steps (a) through (f) for a sufficient number of people of a statistical group to generate statistical database.

* * * * *